United States Patent [19]

Varma et al.

[11] 3,979,417
[45] Sept. 7, 1976

[54] 1 H-ANDROSTA(16,17)CYCLOPENTENE-3-ONES

[75] Inventors: Ravi K. Varma, Belle Mead; Christopher M. Cimarusti, Hamilton, both of N.J.

[73] Assignee: E. R. Squibb & Sons, Inc., Princeton, N.J.

[22] Filed: Nov. 7, 1975

[21] Appl. No.: 630,121

[52] U.S. Cl. .......................................... 260/397.45
[51] Int. Cl.² ............................................. C07J 5/00
[58] Field of Search ............................. 260/397.45; /Machine Searched Steroids

[56] References Cited
OTHER PUBLICATIONS
J. Org. Chem., 33 (1968) p. 3544 (1968).
Ann. Chem., 685, 218 (1965).

*Primary Examiner*—Elbert L. Roberts
*Attorney, Agent, or Firm*—Lawrence S. Levinson; Merle J. Smith; Donald J. Barrack

[57] ABSTRACT

Steroids having the formula

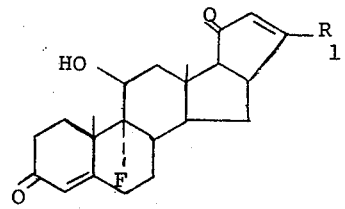

and the 1,2-dehydro derivatives thereof, wherein $R_1$ is phenyl, naphthyl, or substituted phenyl or naphthyl, have useful anti-inflammatory activity.

6 Claims, No Drawings

1 H-ANDROSTA(16,17)CYCLOPENTENE-3-ONES

SUMMARY OF THE INVENTION

Steroids having the formula

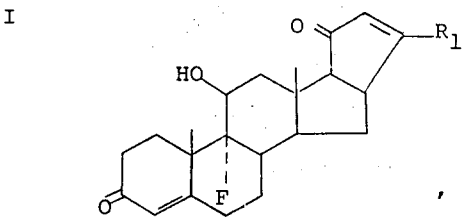

and the 1,2-dehydro derivatives thereof, have useful anti-inflammatory activity. In formula I, and throughout the specification, the symbols are as defined below.

R₁ can be phenyl, naphthyl, or phenyl or naphthyl substituted with one or two alkyl, alkoxy, halogen or dialkylamino groups.

The term "halogen", as used throughout the specification, refers to fluorine, chlorine, bromine and iodine.

The term "alkyl", as used throughout the specification, refers to straight and branched chain alkyl groups having 1 to 7 carbon atoms.

The term "alkoxy", as used throughout the specification, refers to groups having the formula Y-O—, wherein Y is alkyl as defined above.

DETAILED DESCRIPTION OF THE INVENTION

The steroids of formula I, and the 1,2-dehydro derivatives thereof, are physiologically active substances which possess glucocorticoid and anti-inflammatory activity and hence can be used in lieu of known glucocorticoids in the treatment of rheumatoid arthritis, for which purpose they can be administered in the same manner as hydrocortisone, for example, the dosage being adjusted for the relative potency of the particular steroid. In addition, the steroids of this invention can be used topically in lieu of known glucocorticoids in the treatment of skin conditions such as dermatitis, psoriasis, sunburn, neurodermatitis, eczema, and anogenital pruritus.

When given orally, the compounds of this invention may be used in a daily dosage range of 0.1 to 200 milligrams per 70 kilograms, preferably 0.3 to 100 milligrams per 70 kilograms. If administered topically, the compounds of this invention may be used in the range of 0.01 to 5.0% by weight, preferably 0.05 to 2.0% by weight, in a conventional cream or lotion.

The steroids of this invention can be prepared from 16α-aroyl steroids having the formula

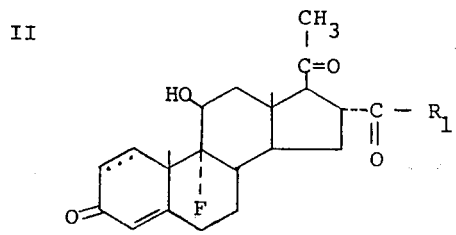

In formula II, and throughout the specification, the dotted line in the 1,2-position of the steroid represents the optional presence of ethylenic unsaturation. The preparation of steroids of formula II is described in copending United States patent application Ser. No. 626,947 filed Oct. 29, 1975. As described therein, the steroids of formula II can be prepared by reacting a benzaldehyde derivative having the formula

with a steroid having the formula

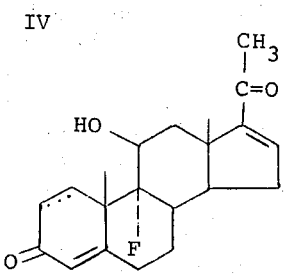

The reaction can be run in a polar organic solvent, e.g., dimethylsulfoxide or dimethylformamide, in the presence of sodium cyanide. The reaction is preferably run in an inert atmosphere at a temperature of from about room temperature to about 50°C.

Reaction of a steroid of formula II with alkali, e.g., sodium or potassium hydroxide, yields the corresponding steroids of formula I or its 1,2-dehydro derivative. The reaction can be run in an organic solvent (e.g., methanol), or combination of organic solvents, and will preferably be run in an inert atmosphere under reflux conditions.

The following examples are illustrative of this invention.

EXAMPLE 1

5'-(4-Chlorophenyl)-9-fluoro-2',3'-dihydro-11β-hydroxy-1'H-cyclopent[16,17]androst-4-ene-3,3'-dione To a solution of 500 mg of 16α-(4-chlorobenzoyl)-9-fluoro-11β-hydroxypregn-4-ene-3,20-dione in 15 ml of methanol and 25 ml of tetrahydrofuran is added dropwise 40% aqueous sodium hydroxide until the pH of the solution is 9–10. The solution is then stirred at 85°C (bath temp.) under nitrogen for 7 hours, cooled, and evaporated in vacuo. The slurry is poured into ice-water and extracted with chloroform. The chloroform solution is washed with 5% hydrochloric acid, dried (over anhydrous sodium sulfate) and evaporated in vacuo. The residue is dissolved in 1:3 hexane-chloroform and chromatographed on a 50 g-silica gel column. Elution with 1:3 hexane-chloroform and 1:4 hexane-chloroform gives 460 mg of material. Two recrystallizations from acetone-hexane give 230 mg of the title compound, melting point 281°–282°C.

EXAMPLE 2

5'-(4-Bromophenyl)-9-fluoro-2',3'-dihydro-11β-hydroxy-1'H-cyclopent[16,17]androst-4-ene-3,3'-dione A solution of 900 mg. of 16α-(4-bromobenzoyl)-9-fluoro-11β-hydroxypregn-4-ene-3,20-dione in a mixture of glyme (20 ml) and methanol (40 ml) is refluxed under an atmosphere of nitrogen. The pH of the solution is brought to 9–10 by the addition of 10 N aqueous sodium hydroxide and the refluxing is continued under nitrogen. After about 72 hours the solution is cooled, neutralized by the addition of 1N hydrochloric acid and concentrated in vacuo. Water is added and the steroid is isolated as a crystalline solid (0.9 g) by extraction with ethyl acetate-chloroform (1:1). Recrystallization of this from ethyl acetate-hexane affords 520 mg. of the title compound, melting point 297°–298°C.

EXAMPLE 3

9-Fluoro-2',3'-dihydro-11β-hydroxy-5'-phenyl-1'H-cyclopent-[16,17]androst-4-ene-3,3'-dione To a solution of 3.68 g of 16α-benzoyl-9-fluoro-11β-hydroxypregn-4-ene-3,20-dione in 300 ml of 1:1 methanoltetrahydrofuran is added dropwise 40% sodium hydroxide until the pH of the solution is 9–10. The solution is then stirred at 85°C under nitrogen for 10 hours, cooled and evaporated in vacuo. The slurry is poured into ice-water and extracted with chloroform. The chloroform solution is washed with 5% hydrochloric acid and water, dried (over anhydrous sodium sulfate) and evaporated in vacuo. The residue is dissolved in 1:4 hexane-chloroform and chromatographed on a 120 g-silica gel column. Elution with 1:4 hexane-chloroform and chloroform gives 2.7 g of solid. Two recrystallizations from acetone-chloroform give 560 mg of the title compound, melting point 290°–291°C.

EXAMPLES 4–10

Following the procedure of Example 1, but substituting the steroid listed in column I below for 16α-(4-chlorobenzoyl)-9-fluoro-11β-hydroxypregn-4-ene-3,20-dione, yields the steroid listed in column II.

What is claimed is:
1. A steroid having the formula

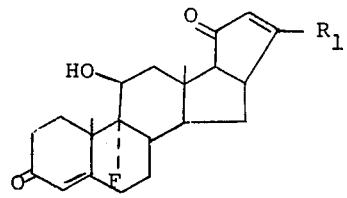

or a 1,2-dehydro derivative thereof, wherein $R_1$ is phenyl, naphthyl, or phenyl or naphthyl substituted with one or two alkyl, alkoxy, halogen, or dialkylamino groups.

2. A steroid in accordance with claim 1 wherein $R_1$ is phenyl or monosubstituted phenyl.

3. A steroid in accordance with claim 1 wherein $R_1$ is phenyl.

4. The steroid in accordance with claim 1 having the name 5'-(4-chlorophenyl)-9-fluoro-2',3'-dihydro-11β-hydroxy-1'H-cyclopent[16,17]androst-4-ene-3,3'-dione.

5. The steroid in accordance with claim 1 having the name 5'-(4-bromophenyl)-9-fluoro-2',3'-dihydro-11β-hydroxy-1'H-cyclopent[16,17]androst-4-ene-3,3'-dione.

6. The steroid in accordance with claim 1 having the name 9-fluoro-2',3'-dihydro-11β-hydroxy-5'-phenyl-1'H-cyclopent[16,17]androst-4-ene-3,3'-dione.

* * * * *

| Example | Column I | Column II |
|---|---|---|
| 4 | 16α-(4-dimethylaminobenzoyl)-9-fluoro-11β-hydroxypregn-4-ene-3,20-dione | 5'-(4-dimethylaminophenyl)-9-fluoro-2',3'-dihydro-11β-hydroxy-1'H-cyclopent[16,-17]androst-4-ene-3,3'-dione |
| 5 | 16α-(2-ethoxybenzoyl)-9-fluoro-11β-hydroxypregn-4-ene-3,20-dione | 5'-(2-ethoxyphenyl)-9-fluoro-2',3'-dihydro-11β-hydroxy-1'H-cyclopent[16,17]androst-4-ene-3,3'-dione |
| 6 | 9-fluoro-11β-hydroxy-16α-(3-methylbenzoyl)pregn-4-ene-3,20-dione | 9-fluoro-2'-3'-dihydro-11β-hydroxy-5'-(3-methylphenyl)-1'H-cyclopent[16,17]androst-4-ene-3,3'-dione |
| 7 | 9-fluoro-16α-(4-fluorobenzoyl)-11β-hydroxypregn-4-ene-3,20-dione | 9-fluoro-5'-(4-fluorophenyl)-2',3'-dihydro-11β-hydroxy-1'H-cyclopent[16,17]androst-4-ene-3,3'-dione |
| 8 | 9-fluoro-11β-hydroxy-16α-(1-naphthoyl)pregn-4-ene-3,20-dione | 9-fluoro-2',3'-dihydro-11β-hydroxy-5'-(1-naphthyl)-1'H-cyclopent[16,17]androst-4-ene-3,3'-dione |
| 9 | 9-fluoro-11β-hydroxy-16α-(2-naphthoyl)pregn-4-ene-3,20-dione | 9-fluoro-2',3'-dihydro-11β-hydroxy-5'-(2-naphthyl)-1'H-cyclopent[16,17]androst-4-ene-3,3'-dione |
| 10 | 16α-(4-bromobenzoyl)-9-fluoro-11β-hydroxypregna-1,4-diene-3,20-dione | 5'-(4-bromophenyl)-9-fluoro-2',3'-dihydro-11β-hydroxy-1'H-cyclopent[16,17]androsta-1,4-diene-3,3'-dione |